United States Patent [19]

Crosby

[11] 4,067,862

[45] Jan. 10, 1978

[54] PROCESS FOR MODIFICATION OF POLYMERIC MATERIALS WITH A NITRILE SULPHIDE

[75] Inventor: John Crosby, Runcorn, England

[73] Assignee: Imperial Chemical Industries Limited, United Kingdom

[21] Appl. No.: 716,454

[22] Filed: Aug. 23, 1976

[30] Foreign Application Priority Data

Aug. 26, 1975 United Kingdom ............... 35206/75
Sept. 19, 1975 United Kingdom ............... 38551/75
Oct. 31, 1975 United Kingdom ............... 45325/75

[51] Int. Cl.$^2$ .......................... C08J 3/24; C08K 5/35; C08K 5/43; C08K 5/47
[52] U.S. Cl. .............................. 260/79.5 P; 260/2.5 R; 260/2.5 H; 260/2.5 L; 260/2.5 N; 260/75 S; 260/79.5 C; 260/775; 260/785
[58] Field of Search ................. 260/775, 785, 79.5 C, 260/79.5 P, 2.5 R, 2.5 H, 2.5 L, 2.5 N, 75 S

[56] References Cited

U.S. PATENT DOCUMENTS

| | | | |
|---|---|---|---|
| 3,026,305 | 3/1962 | Robinson | 260/785 |
| 3,175,992 | 3/1965 | Anderson | 260/785 |
| 3,502,626 | 3/1970 | Dall'Asta et al. | 260/79.5 P |
| 3,531,425 | 9/1970 | Burk et al. | 260/22 R |
| 3,976,605 | 8/1976 | Matsunaga et al. | 260/2.5 R |
| 3,979,369 | 9/1976 | Trivette | 260/79.5 C |

OTHER PUBLICATIONS

Howe et al., Journal of the Chemical Society, Chemical Communications, vol. 15, 1973, pp. 524–525.

*Primary Examiner* — Ronald W. Griffin
*Attorney, Agent, or Firm* — Cushman, Darby & Cushman

[57] ABSTRACT

Process for the modification, e.g. cross-linking, of polymers containing C=C or C≡C unsaturation by reacting them with nitrile sulphides or precursors therefor. A preferred system entails mixing the polymer with a 5-R-substituted-1,3,4-oxathiazol-2-one and heating the mixture to a temperature at which the nitrile sulphide is generated.

6 Claims, No Drawings

PROCESS FOR MODIFICATION OF POLYMERIC MATERIALS WITH A NITRILE SULPHIDE

This invention relates to the modification, and especially the cross-linking, of polymeric materials containing C=C or C≡C unsaturated groups by reaction with a nitrile sulphide.

According to the present invention, a process for the modification of a polymeric material containing at least one C=C or C≡C unsaturated group in its molecule comprises reacting said polymeric material with a nitrile sulphide of formula (CNS)$_2$ or R—(CNS)$_n$ where R represents an organic radical which is inert to the nitrile sulphide group or its precursors and $n$ is an integer $\geq 1$.

In the context of this specification, the term "modification" is intended to include cross-linking, chain extension and the bonding of additive groups to the polymer molecule. In the case of cross-linking there must be at least two unsaturated groups in the polymer molecule.

Suitable monovalent organic radicals R include alkyl, cycloalkyl, aryl, aralkyl and alkaryl, such as methyl, ethyl, propyl, butyl, hexyl, cyclohexyl, phenyl, naphthyl, biphenyl, anthryl, phenylethyl, tolyl and benzyl. Suitable divalent radicals include alkylene, cycloalkylene, arylene, aralkylene, alkarylene, alkylene-diarylene, cycloalkylene-dialkylene and arylene-dialkylene. Examples of radicals R include phenyl, p-chlorophenyl, methyl, ethyl, cyclohexyl, biphenyl, naphthyl, methylene, ethylene, trimethylene, tetramethylene, hexamethylene, decamethylene and cyclohexylene. The radicals may also include oxygen atoms, for example, alkyleneoxy-alkylene or alkylene-oxy-arylene and corresponding thio radicals. R may also comprise a sulphone, for example ethylene-sulphonyl-ethylene. R may also contain other hetero atomic groups, provided these are inert to the nitrile sulphides or their precursors.

The maximum value of $n$ is dependent on the valency of radical R which it cannot, of course, exceed.

It is believed, without prejudice to the invention, that a dual cross-linking mechanism may obtain with the system described here. In the first instance the nitrile sulphides may react with unsaturated groupings in a manner analogous to the well known 1,3 dipolar addition reactions of nitrile oxides with multiple bonds (cf. C GRUNDMANN & P GRUNANGER, "THE NITRILE OXIDES", Springer-Verlag, Berlin, 1971)

Secondly, however, the nitrile sulphide groups may decompose and so act as sulphur generators, the sulphur produced then acting as the cross-linking agent. Clearly, therefore, any nitrile sulphide or nitrile sulphide precursor may function as a cross-linking agent either through reaction of the intact nitrile sulphide groups when two or more are present per molecule of cross-linking agent or through the production of sulphur, which then proceeds to effect the cross-link, or by a combination of these effects. The exact balance which pertains in a given cross-linking situation will thus depend on the relative rates of reaction of the nitrile sulphide groups as intact groups and their decomposition to afford sulphur.

Because of their reactivity it is preferred that the nitrile sulphides are generated in situ in the presence of the polymeric material. Any suitable process may be used for generating the nitrile sulphides. One especially convenient process involves the thermolysis of 5-R-substituted-1,3,4-oxathiazol-2-ones, as described by R K Howe and J E Franz in *J.C.S Chem Comm* (1973) page 524.

The above-mentioned precursors may be prepared by the action of chlorocarbonyl sulphenyl chloride on the appropriate carboxamide according to the following general reaction

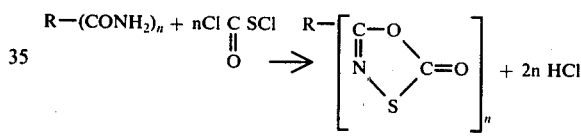

as described in Belgian Pat. No. 680,644.

Another convenient method for their preparation comprises the hydrolysis of trichloromethylsulphonyl amides (A Senning & P Kelly, *Acta Chem. Scand.*, (1967) 1871 21) by heating with 4:1, formic acid:water mixture.

Examples of suitable precursors include

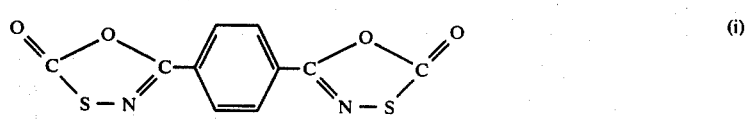

(i)

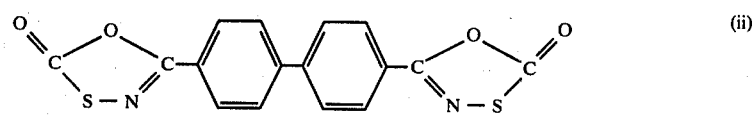

(ii)

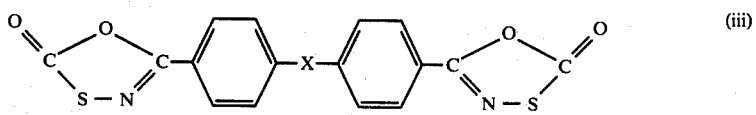

(iii)

(where X=S, SO, SO$_2$, O, CO or CH$_2$)

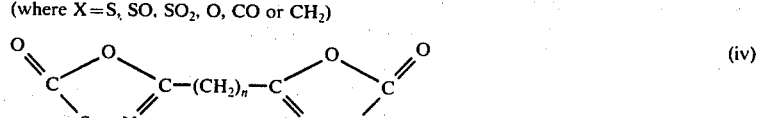

(iv)

(where n is an integer from 1 to 10)

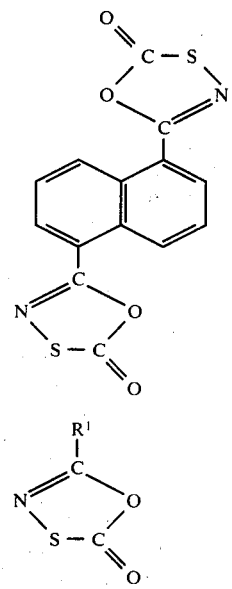

(v)

(vi)

where R¹ is phenyl, p chlorophenyl, methyl or naphthyl.

Thermolysis of precursors of the above types may be accomplished by heating them to a temperature in the range 100° to 200° C, the optimum temperature being dependent on the precise nature of the precursor.

Polymeric materials which may be modified and, especially, cross-linked by the process of the present invention include polybutadiene-1,2
polybutadiene-1,4
styrene-butadiene copolymers
butyl rubber (isobutylene-isoprene copolymers)
natural rubber
polyester resins such as maleate containing polyesters
butadiene-acrylonitrile copolymers
styrene-butadiene-acrylonitrile copolymers
ethylene-propylene-diene terpolymers (the so-called EPDM rubbers)
polychloroprene
polyisoprene
alkyd resins such as tall oil alkyd resins
allyl glycidyl ether-propylene oxide copolymers
polymers containing acetylenic unsaturation, and
mixtures or blends of two or more of such unsaturated polymers.

When used for cross-linking polymeric materials, the present invention is conveniently carried out by mixing a nitrile sulphide precursor intimately with the polymeric material and subsequently heating the mixture to generate the nitrile sulphide and, hence, cross-link the polymer. Mixing of precursor and polymer is readily achieved using conventional rubber mixing techniques.

The amount of precursor which is mixed with the polymer depends mainly upon the degree of cross-linking desired; but generally from 0.01 to 20% by weight of precursor is added, calculated on the weight of polymer. Preferably at least 0.2% of precursor is added.

Once the polymer and nitrile sulphide precursor have been thoroughly mixed, the mixture may be heated to effect cross-linking, usually in the temperature range 100° to 200° C; but temperatures over a wider range may be used, provided the temperature is sufficient to generate the nitrile sulphide but not so great as to cause undue degradation of the polymeric materials.

Additional ingredients may be mixed into the polymer before curing, if desired. Examples of such ingredients include common rubber additives, such as extenders, fillers, pigments, plasticisers and stabilisers.

When our preferred oxathiazolone nitrile sulphide precursors are used, carbon dioxide will be liberated during generation of the nitrile sulphide. This may either be used to advantage as a "blowing agent" to produce foamed materials or alternatively a suitable filler (e.g. barium oxide) may be incorporated in the mixture to absorb the carbon dioxide. It may not be necessary to remove the evolved $CO_2$ chemically; for example, especially when high surface area fillers such as carbon black are present, the $CO_2$ may be absorbed within the polymer, simply by effecting the cross-linking reaction under pressure. Thus one rubber/cross-linking agent formulation may be used to produce foamed or solid rubber articles, depending on whether the formulation is contained in an enclosed space or left open during curing.

The cross-linked polymers resulting from the process of the present invention possess much better tensile properties than before cross-linking, and are substantially insoluble in water and hydrocarbons. The cross-linked polymers may be used in various applications, such as decorative or protective coatings for a variety of substrates, e.g. wood, metal, concrete, paper and plastics and as ingredients for vehicle tyres, hoses and other rubber articles.

Although our process has been mainly described with reference to cross-linking, as previously mentioned, it may also be used to bond additives containing suitable functional groups to polymeric materials containing $C=C$ and $C\equiv C$ unsaturation. Examples of such additives include dyestuffs, antistatic agents, anti-oxidants and reinforcing agents. Examples of reinforcing agents are polyester, nylon, glass and carbon fibres or particulate fillers such as carbon black or fumed silica, the surfaces of which contain, either as a result of their method of preparation, or as a result of subsequent treatment, groups reactive towards nitrile sulphide or sulphur. However, such reactive groups need not be the same as those on the polymeric material.

The invention will be illustrated by the following Examples, in which all parts are by weight.

Preparation of Nitrile Sulphide Precursors

A. 5,5'-ethylene-bis-1,3,4-oxathiazol-2-one

Succinamide in toluene was reacted with two molar equivalents of chlorocarbonylsulphenyl chloride at 90° C. When evolution of HCl had ceased the mixture was heated at reflux for a further 6.5 hours to complete the reaction. The toluene solvent was removed under reduced pressure to afford a residue of crude 5,5'-ethylene-di-1,3,4-oxathiazol-2-one

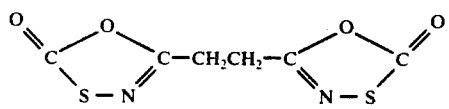

Recrystallisation from acetic or trifluoroacetic acid afforded the pure oxathiazolone MPt 165° (decomp).

B. 5,5'-Methylene-bis-1,3,4-oxathiazol-2-one

This was prepared from malonamide using a similar procedure to that given under A above.

C. 5-(4'chlorophenyl)-1,3,4-oxathiazol-2-one

To chlorocarbonylsulphenyl chloride (90.6 parts) in 1,4-dioxan (360 parts) was added 4-chlorobenzamide (72 parts) and the mixture was then heated at 90° C for 3 hours by which time all the amide had reacted and entered into the solution. Evaporation of the solvent afforded an almost quantitative yield of the oxathiazolone, m pt. 130°–132° C (Reported 127–130°, A senning & P Kelly, *Acta Chem. Scand.*, 21 1871 (1967)).

D. 5-Phenyl-1,3,4-oxathiazol-2-one

Perchloromethyl mercaptan (18.6 parts) was added to dioxan (60 parts) followed by benzamide (12.1 parts) and the mixture was heated at reflux until evolution of HCl ceased. The reaction mixture was evaporated to dryness and to the resulting crude N-(trichloromethylsulphenyl) benzamide was added 80% formic acid. Heating for 2 hours at 80° C followed by cooling afforded crystals of the required oxathiazolone (6.4 parts) m pt. 68° C (lit, Senning & Kelly loc cit, mp 68.5°–70°).

EXAMPLE 1

5,5'-Ethylene-bis-1,3,4-oxathiazol-2-one (6 parts) was mixed with styrene butadiene rubber (100 parts) and HAF carbon black (50 parts) on a conventional rubber mill. Examination of the compounded rubber on a Wallace-Shawbury Curemeter showed that a good cure could be effected in less than 2 minutes at 180° C or in approximately 15 minutes at 160° C. A sample of the rubber compound was then cured under pressure at 160° C for 15 minutes to give a rubber which was essentially free of voids and which had a tensile strength of 1100 psi and elongation at break of 450%. A further sample of the rubber was cured in an open mould at 180° C for 15 minutes and produced a self-skinned, uniformly foamed rubber.

EXAMPLE 2

5,5'-Ethylene-bis-1,3,4-oxathiazol-2-one (10 parts), barium oxide (15 parts) and carbon black (50 parts) were milled into a styrene-butadiene rubber. The resulting rubber compound was cured under pressure at 180° C for 10 minutes to give a piece of rubber which was substantially free of voids.

EXAMPLE 3

The procedure of Example 1 was repeated except that 5,5'-methylene-bis-1,3,4-oxathiazol-2-one was employed. As in Example 1, a solid rubber was obtained when the curing took place under pressure but a foamed rubber product was obtained when curing was allowed to take place in an open mould.

EXAMPLE 4

5-(4'-Chlorophenyl)-1,3,4-oxathiazol-2-one (10 parts) and HAF carbon black (50 parts) were mixed into a styrene-butadiene rubber on a conventional rubber mill. The resulting rubber compound was cross-linked by heating at 170° C for 25 minutes.

EXAMPLE 5

The procedure of Example 4 was repeated except that an EPDM rubber which contained about 7½% w/w ethylidene norbornene as termonomer was used in place of the SBR. The resulting rubber compound was cross-linked by heating at 170° C for 20 minutes.

EXAMPLE 6

5-Phenyl-1,3,4-oxathiazol-2-one (10 parts) and HAF carbon black (50 parts) were mixed into a styrene-butadiene rubber (100 parts). This rubber compound was cured in a press, heated to 175° C, for 25 minutes to give a product with tensile strength 3000 psi. The same compound was cured in an open mould at 175° C for 25 minutes to give a tough, self-skinned foam.

EXAMPLE 7

The procedure of Example 6 was repeated except that instead of the styrene butadiene rubber the EPDM rubber of Example 5 was used. The results were substantially as in Example 6 except that the degree of foaming was less.

What we claim is:

1. A process for the modification of a polymeric material containing at least one C=C unsaturated group in its molecule, in which the said polymeric material is reacted with a nitrile sulphide of formula

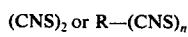

where R represents an organic radical which is inert to the nitrile sulphide group and n is an integer ≧1.

2. A process as claimed in claim 1 in which the polymeric material is mixed with a precursor for the said nitrile sulphide comprising a 5-R-substituted-1,3,4-oxathiazol-2-one and the mixture heated to a temperature at which the nitrile sulphide is generated.

3. A process as claimed in claim 2 in which the nitrile sulphide precursor is selected from the group consisting of oxathiazoles having the formulae

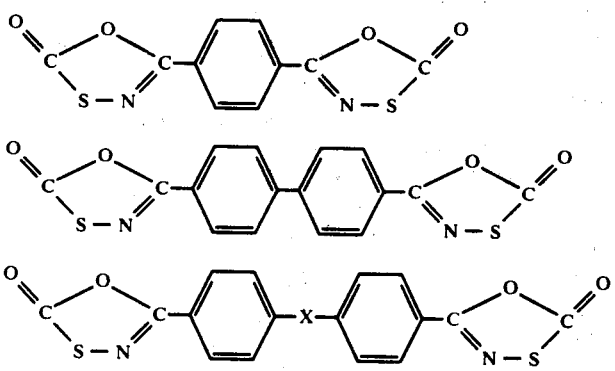
(i)

(ii)

(iii)

(where X=S, SO, SO₂, O, CO or CH₂)

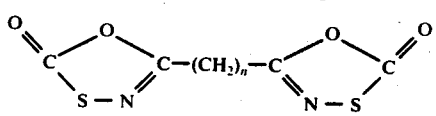
(iv)

(where n is an integer from 1 to 10)

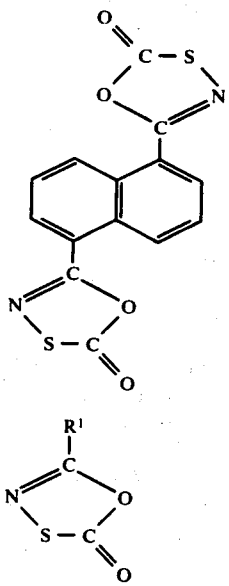
(v)

(vi)

where R¹ is phenyl, p chlorophenyl, methyl or naphthyl.

4. A process as claimed in claim 2 in which the mixture is heated to a temperature in the range 100° to 200° C.

5. A process as claimed in claim 2 in which from 0.1 to 20% by weight of precursor is added to the polymeric material.

6. A process as claimed in claim 1 in which the polymeric material is a natural or synthetic rubber.

* * * * *